(12) United States Patent
Suh et al.

(10) Patent No.: US 11,224,376 B2
(45) Date of Patent: Jan. 18, 2022

(54) TINNITUS TESTING DEVICE USING BRAIN WAVES AND TINNITUS TESTING METHOD USING SAME

(75) Inventors: Myung Whan Suh, Chungcheongnam-do (KR); Il Yong Park, Chungcheongnam-do (KR); Seung Ha Oh, Seoul (KR); Chung Ku Rhee, Chungcheongnam-do (KR); Phil Sang Chung, Chungcheongnam-do (KR)

(73) Assignee: Industry-Academic Cooperation Foundation, Dankook University, Gyeonggi-do (KR)

( * ) Notice: Subject to any disclaimer, the term of this patent is extended or adjusted under 35 U.S.C. 154(b) by 1156 days.

(21) Appl. No.: 13/976,395

(22) PCT Filed: Apr. 29, 2011

(86) PCT No.: PCT/KR2011/003188
§ 371 (c)(1),
(2), (4) Date: Sep. 9, 2013

(87) PCT Pub. No.: WO2012/121450
PCT Pub. Date: Sep. 13, 2012

(65) Prior Publication Data
US 2013/0338527 A1    Dec. 19, 2013

(30) Foreign Application Priority Data
Mar. 4, 2011 (KR) .................. 10-2011-0019599

(51) Int. Cl.
*A61B 5/12* (2006.01)
*A61B 5/374* (2021.01)
(Continued)

(52) U.S. Cl.
CPC ............ *A61B 5/374* (2021.01); *A61B 5/128* (2013.01); *A61B 5/316* (2021.01); *A61B 5/38* (2021.01)

(58) Field of Classification Search
CPC ........................... A61B 5/04845; A61F 11/00
See application file for complete search history.

(56) References Cited

U.S. PATENT DOCUMENTS

| | | | |
|---|---|---|---|
| 2006/0167376 A1* | 7/2006 | Viirre | A61B 5/0482 600/559 |
| 2009/0163828 A1* | 6/2009 | Turner | A61B 5/04845 600/559 |
| 2010/0076338 A1 | 3/2010 | Kwak | |

OTHER PUBLICATIONS

Harris, Kelly C., et al. "Electrophysiologic Correlates of Intensity Discrimination In Cortical Evoked Potentials of Younger and Older Adults", NIH Public Access Hear Res. Author manuscript; available in PMC Dec. 1, 2007 (Published in final edited form as: Hear Res. Jun. 2007; 228(1-2): 58-68.).

* cited by examiner

Primary Examiner — Rajeev P Siripurapu
Assistant Examiner — Michael A Catina
(74) Attorney, Agent, or Firm — Seed IP Law Group LLP

(57) ABSTRACT

The tinnitus testing apparatus of this invention comprises a control part that in turn comprises: an auditory stimulus generation part that can generate a stimulus; and an AEP acquisition and amplitude measurement part that can acquire auditory evoked potential (AEP) brain waves of a examinee due to said stimulus and measure the specific amplitude of said acquired brainwaves; wherein said auditory stimulus is one or more of: a 1st stimulus containing continuous noise and pulse noise; and a 2nd stimulus containing pulse noise and continuous noise with a silent gap.

7 Claims, 10 Drawing Sheets

(51) Int. Cl.
*A61B 5/38* (2021.01)
*A61B 5/316* (2021.01)

[Figure 1]
(a)
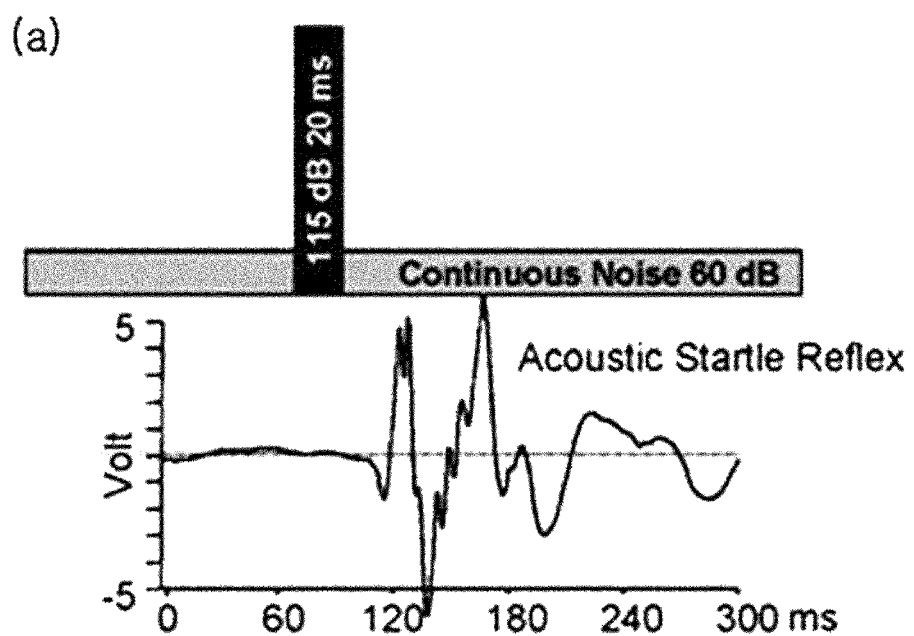
(b)
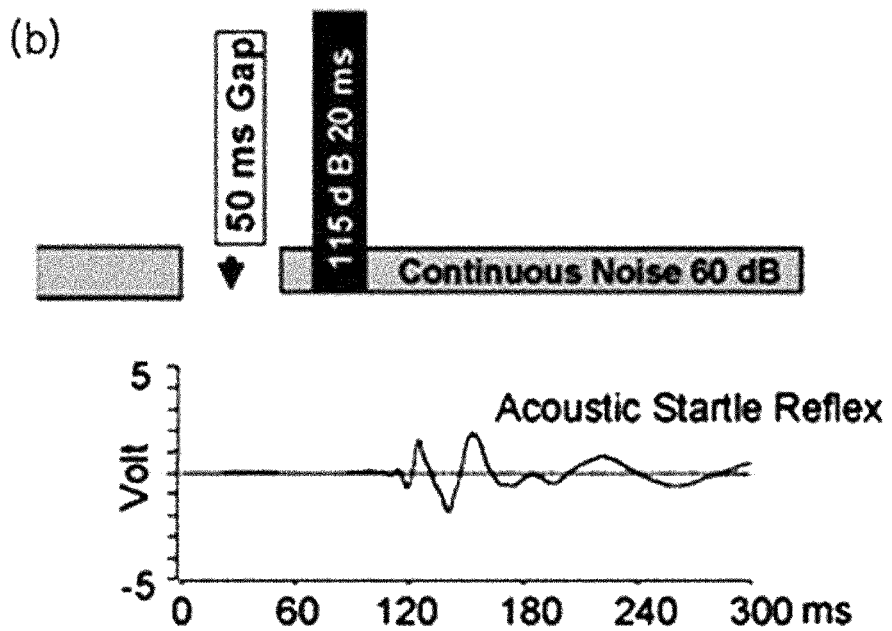

[Figure 2]
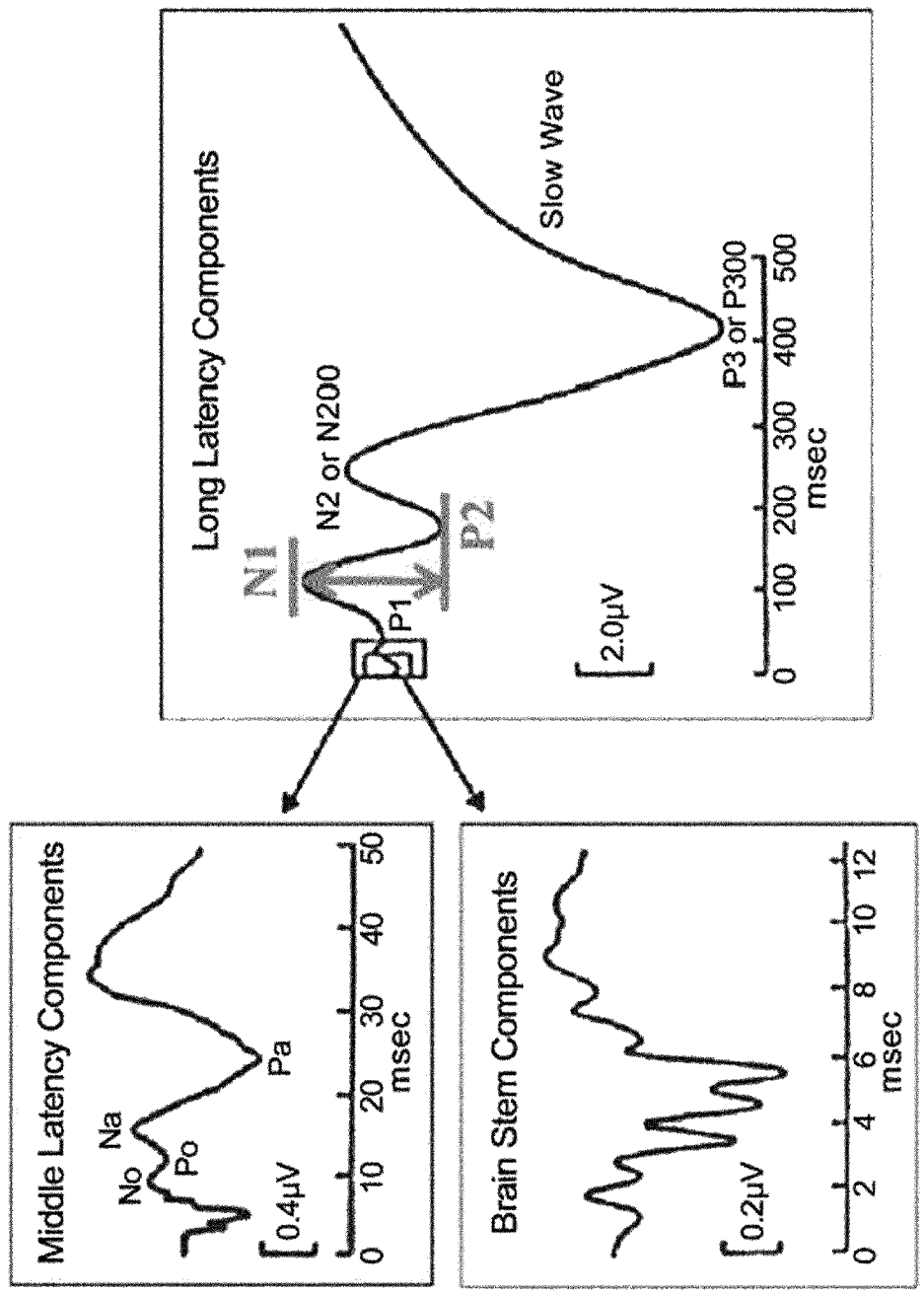

[Figure 3]
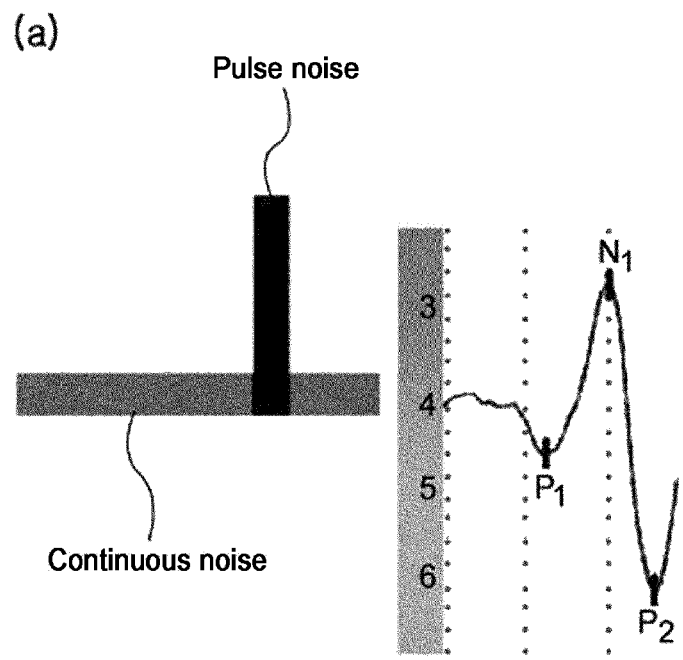
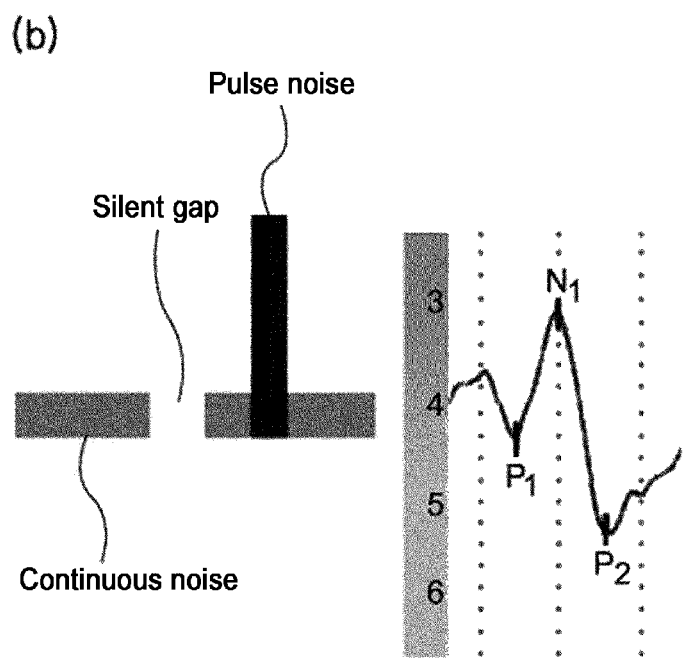

【Figure 4】
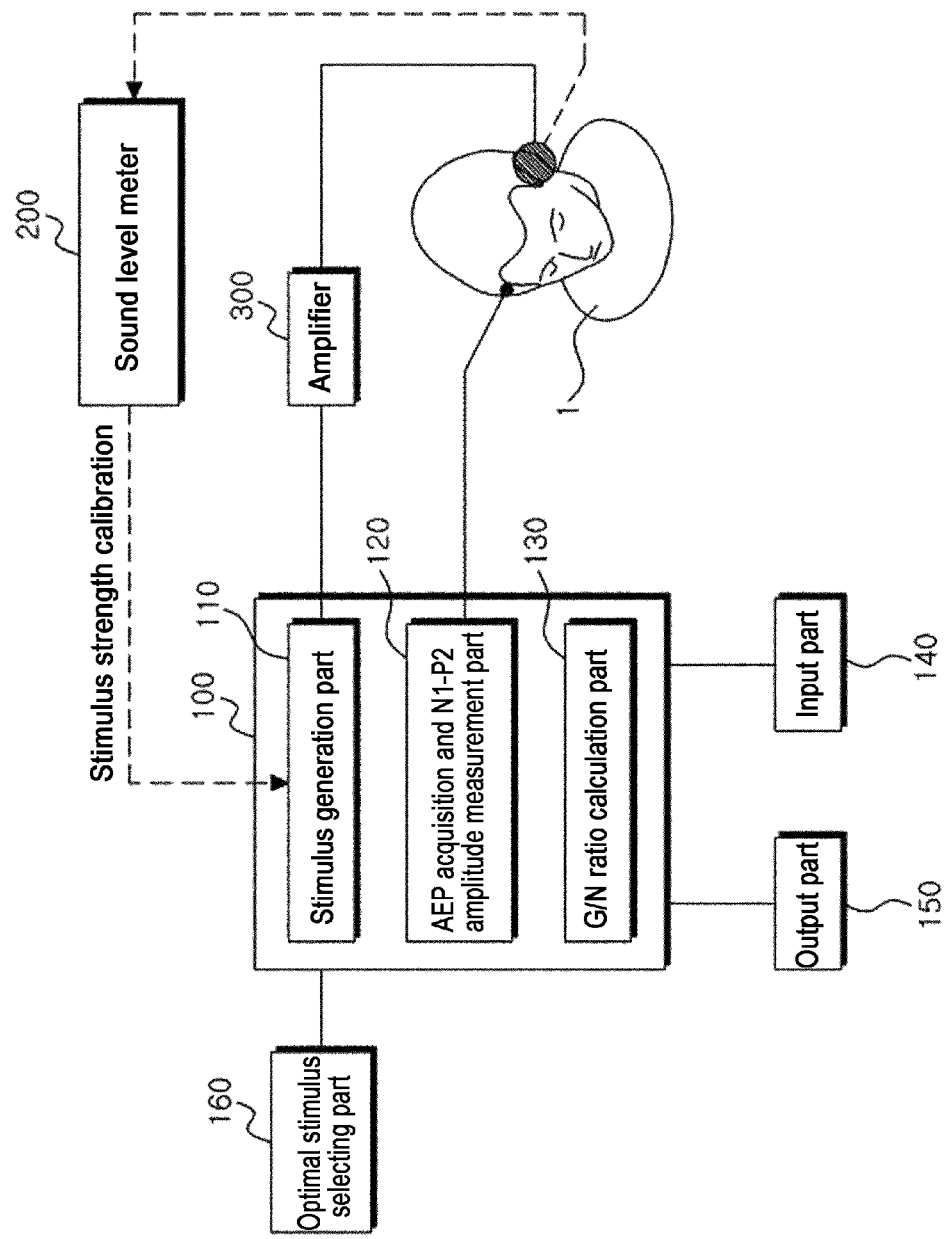

[Figure 5]
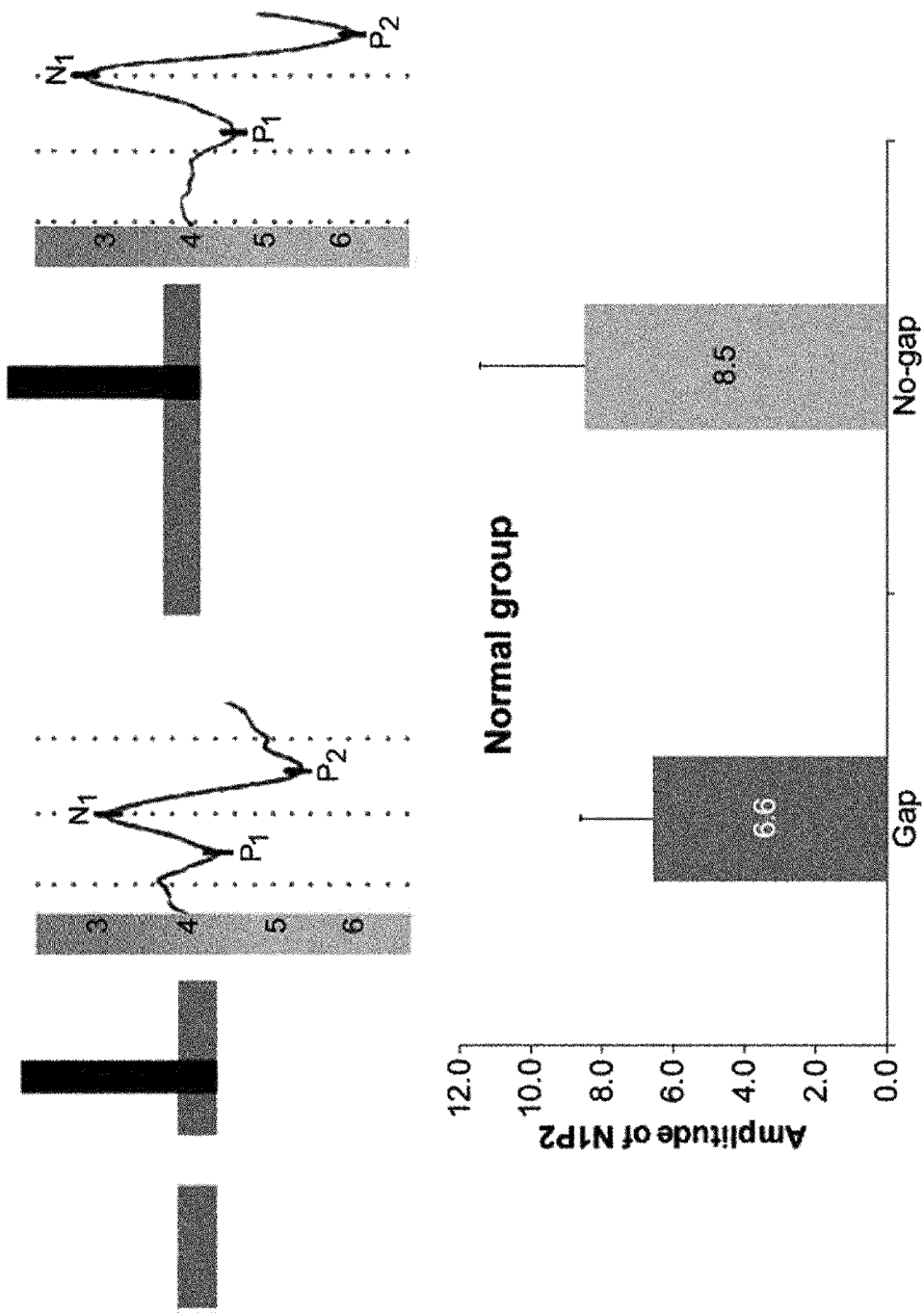

[Figure 6]
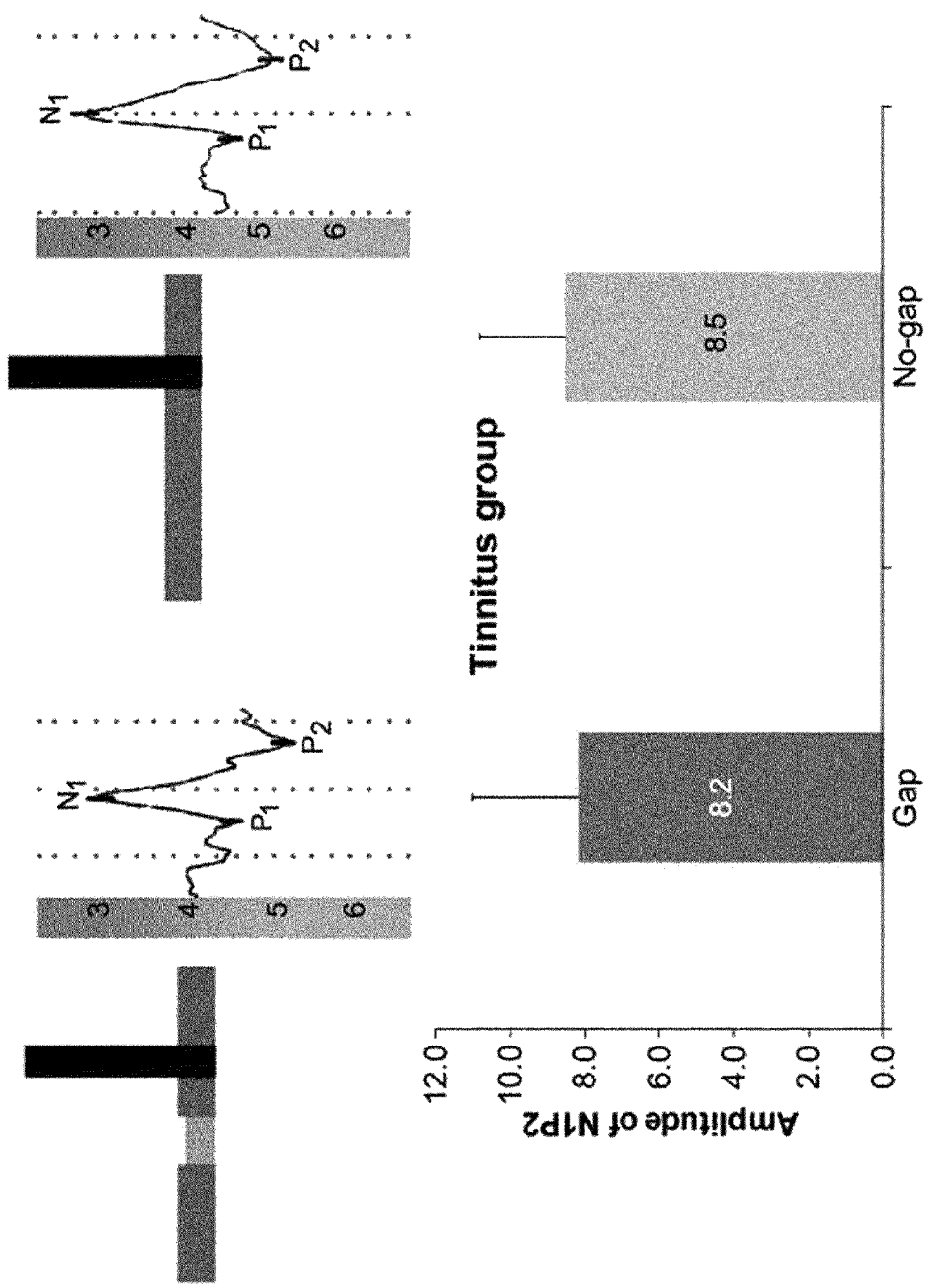

[Figure 7]
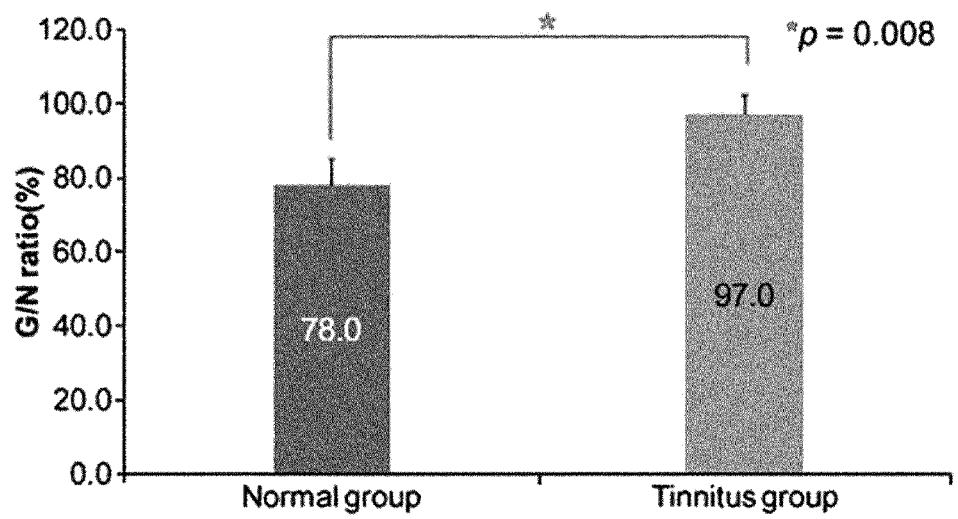

[Figure 8]
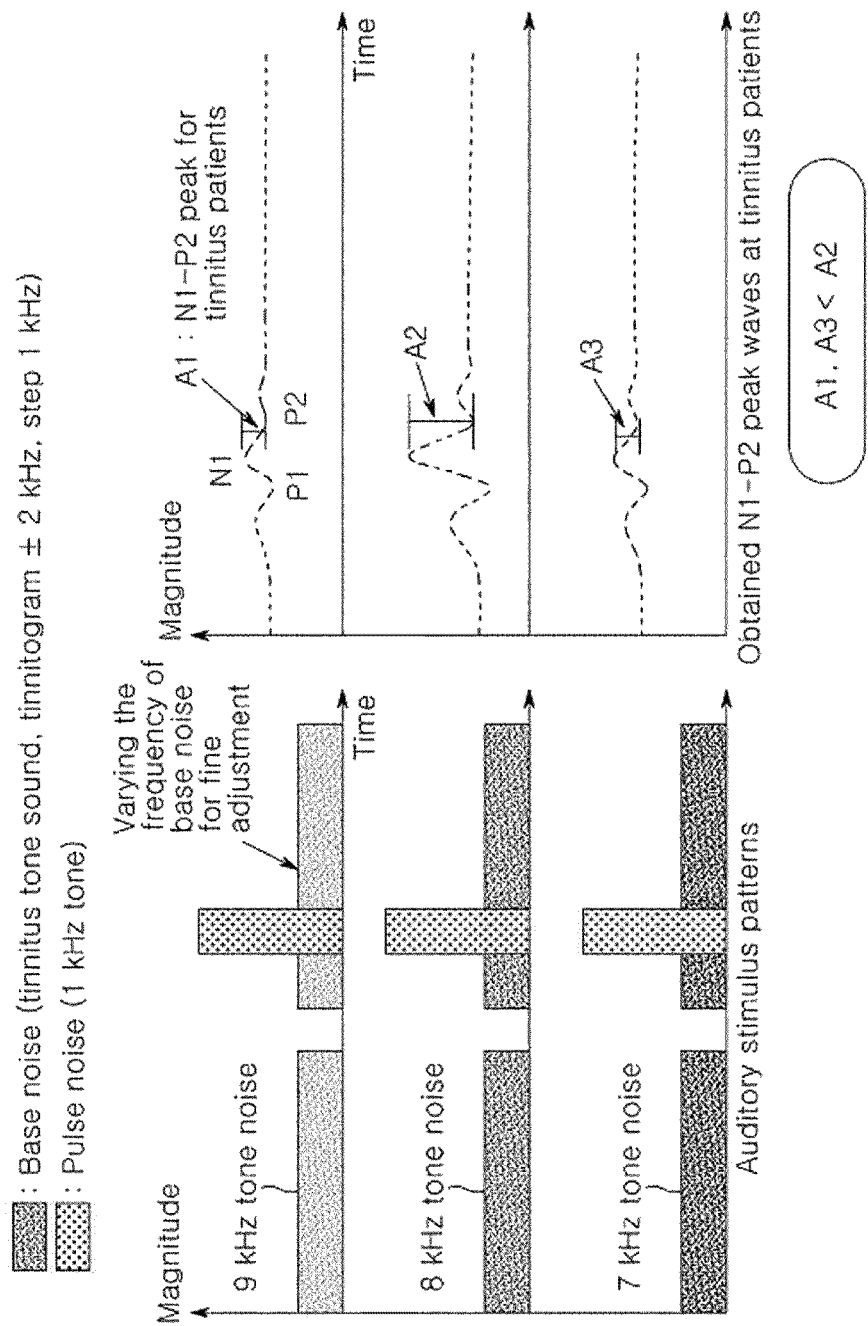

【Figure 9】
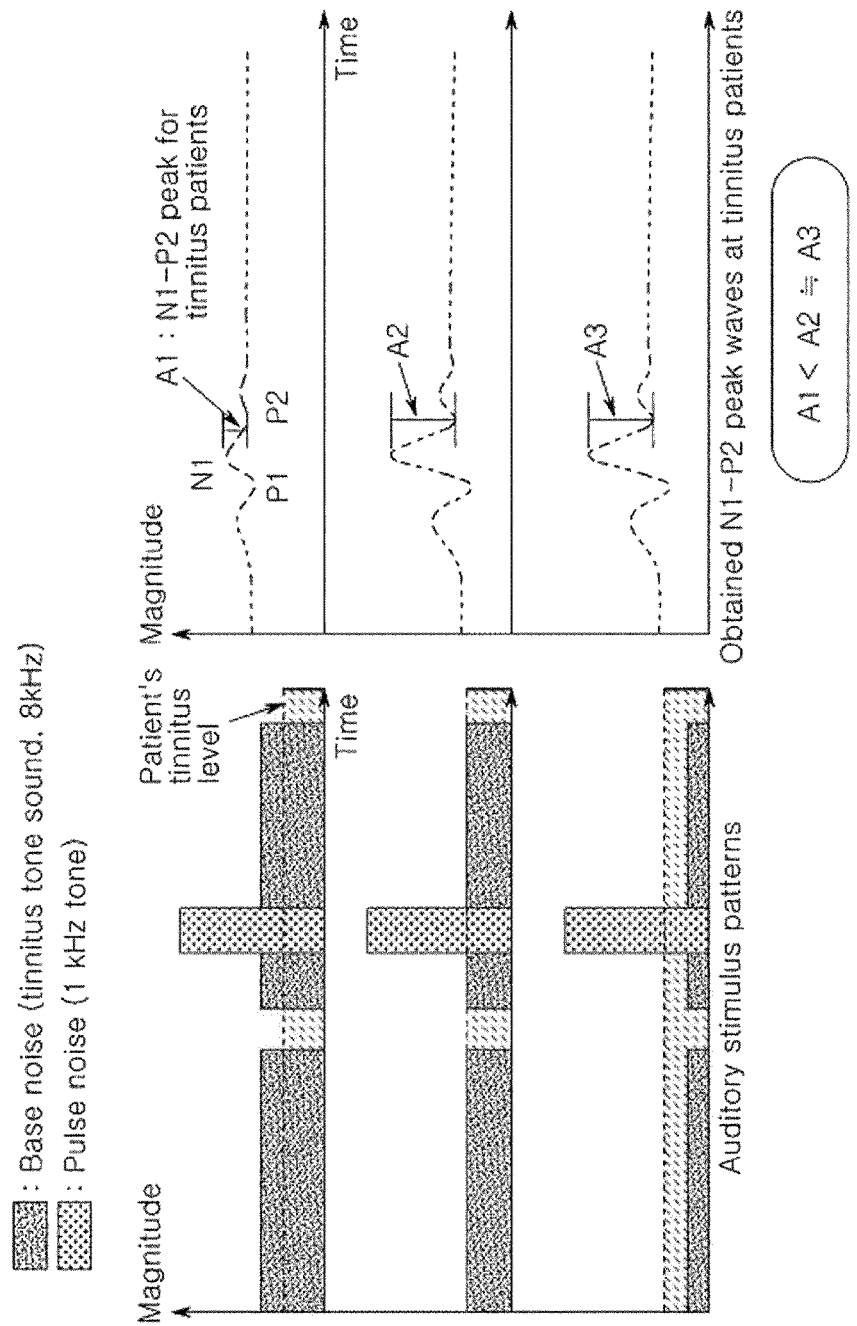

[Figure 10]
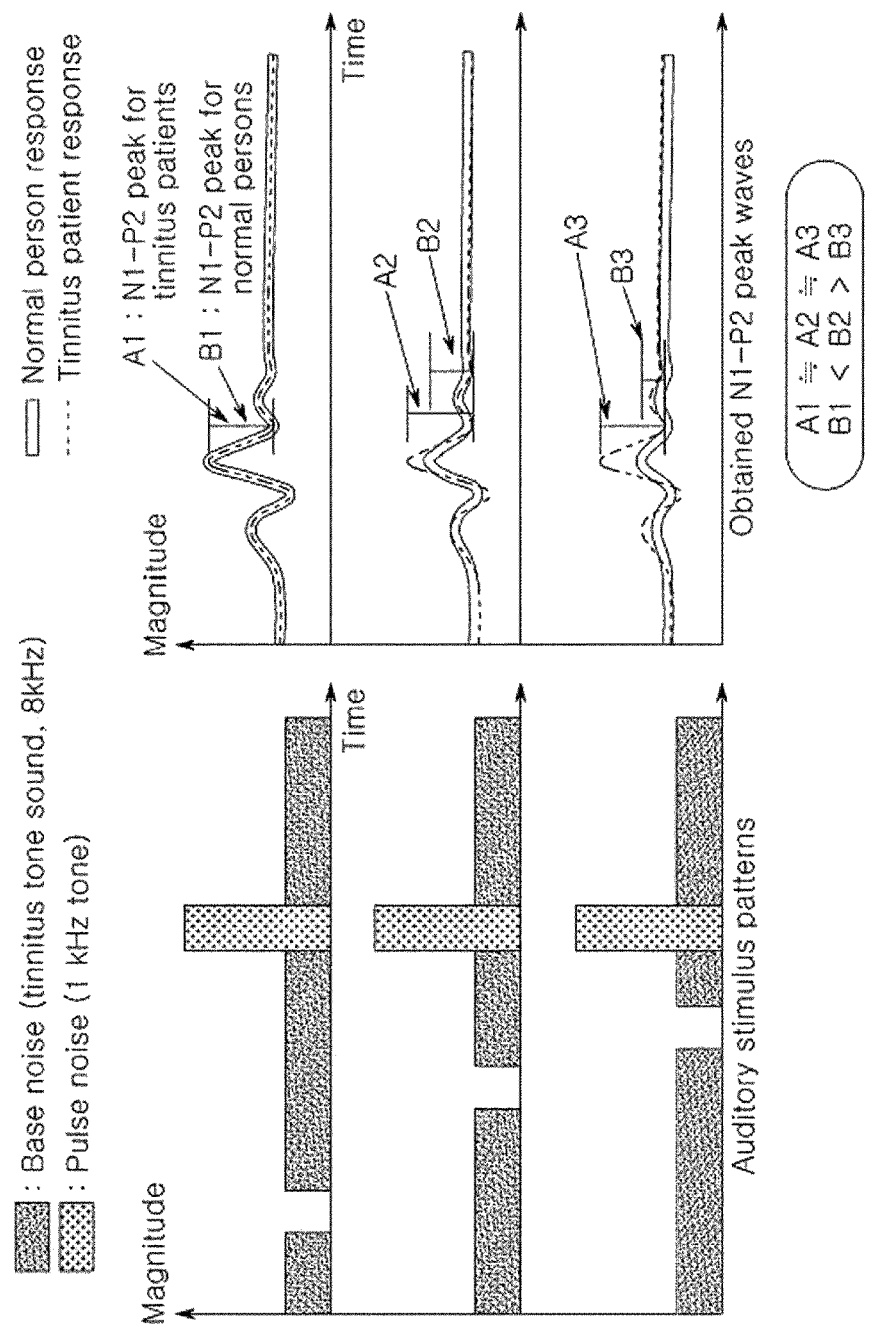

TINNITUS TESTING DEVICE USING BRAIN WAVES AND TINNITUS TESTING METHOD USING SAME

TECHNICAL FIELD

This invention relates to a tinnitus testing apparatus using brain waves and testing method for verification of tinnitus using same; more specifically, it relates to a testing apparatus that, compared to subjective methods based on examinee cooperation, can more objectively prove whether tinnitus is present by measuring the brain waves of the examinee, and to a method of testing for tinnitus using this apparatus.

BACKGROUND ART

"Tinnitus" refers to the subjective sensation of hearing noise in one's ears. Specifically, it is the state of feeling that one is hearing a sound in the absence of any external auditory stimulus. In a quiet fully soundproofed room, 95% of ordinary persons experience tinnitus of 20 dB (decibels) or less, but this is not referred to clinically as tinnitus; "tinnitus" refers to cases in which noise or sound is heard at a level sufficient to perturb the examinee.

Specifically, tinnitus of this kind can be classified as two types: the first is subjective tinnitus, which is heard or perceived only by the examinee, and the second is objective tinnitus, which is a physical sound occurring within the person's body and can be heard by others. Subjective tinnitus accounts for the majority of cases of tinnitus; illnesses causing subjective tinnitus include sudden hearing loss, Meniere's disease, noise-induced hearing loss, head injury, age-related hearing loss, ototoxic drugs, acoustic tumor, or middle-ear infection; in addition, tinnitus frequently occurs in the absence of any particular disease, following overwork or stress.

Tinnitus with a severity such as to cause severe difficulty sleeping occurs in about 8% of cases, and tinnitus causing extreme impairment such as to make daily life difficult occurs in about 1% of cases. Patients who complain of tinnitus may have difficulty with daily life if suffering severely from different sounds in their ears or head. In current society, despite the gradual upward trend in tinnitus patients as the frequency of exposure to noise has increased, tinnitus is still thought of as an incurable disease that is difficult to treat. For this reason, demand is mounting for accurate diagnosis and treatment of tinnitus.

Accordingly, there is a need for a method whereby the presence or absence of tinnitus can be objectively proven or verified.

Turner et al. have presented a method whereby the presence or absence of tinnitus can be immediately verified in animals without a separate training period, terming this "gap pre-pulse inhibition of acoustic startle (GPIAS)". This is a method using the fact that when an auditory stimulus is applied in a specific sequence, the startle reflex differs in animals depending on whether tinnitus is present.

Referring to FIG. 1, the GPIAS proposed by Turner et al. can be described as follows.

FIG. 1(a) is a graph measuring the startle reflex in animals for auditory stimulus with no silent gap; FIG. 1(b) is a graph measuring the startle reflex in animals for auditory stimulus with a silent gap.

As shown in FIG. 1, if uninterrupted continuous noise is provided, the startle reflex for pulse noise is measured very high, but if interrupted noise is provided, the startle reflex is measured lower due to the nervous system having prepared for the pulse noise after the interruption. (Here, continuous noise has a magnitude of about 60 dB, and pulse noise has a magnitude of about 115 dB for 20 ms; the silent gap was kept to 50 ms, and notably, a piezoelectric transducer was used for measurement of the startle reflex.)

The GPIAS using the above principles uses an apparatus that measures the movement of the animal quantitatively by means of a piezoelectric transducer (apparatus that converts applied pressure to electrical energy by means of the piezoelectric phenomenon, whereby pressure creates a difference in electric potential). The animal's body is then fixed in position so that it cannot move, and a pressure sensor is used to measure only the physical movement due to the animal's startle reflex.

Reviewing the measurement method, a continuous noise is applied at a 60 dB SPL (sound pressure level) at first, and then a silent gap of approximately 50 ms is applied, whereupon a pulse sound of approximately 20 ms and 115 dB is applied.

As the result of this method of measurement, if the animal does suffer from tinnitus, the silent gap will be filled by tinnitus, and therefore the animal will not perceive there to have been a silent gap, and thus a large startle reflex will be measured (similar to the result shown in FIG. 1(a)); in contrast, if the animal is free of tinnitus, then because it recognizes there to have been a silent gap, the measured startle reflex will be relatively slight (similar to the result shown in FIG. 1(b)).

Research findings whereby the presence or absence of tinnitus in animals could be measured effectively using GPIAS as above have been steadily increasing since 2006; currently, GPIAS is well-known among researchers as a method that is comparatively widely used to measure the presence or absence of tinnitus in animals.

However, to date, there have been no reports of inventions applying the above-described principles to the testing of humans. The tinnitogram currently being used on humans is a subjective testing method; it has the advantage of enabling comparatively simple and straightforward diagnosis of tinnitus. However, because it is a subjective testing method that depends on the cooperation of the examinee exposed to an auditory stimulus, there are considerable problems in the testing of elderly and infants who have insufficient understanding of the test procedure. In addition, it is not easy to ensure objectively with respect to the determination of tinnitus when it is linked to problems of financial compensation of an examinee in whom tinnitus has occurred due to an accident or noise exposure.

Therefore, the present inventors have invented an apparatus for tinnitus testing using brainwaves, and a testing method using same, whereby the presence or absence of tinnitus can be objectively determined in humans, by further improving the above-described method of testing for tinnitus in animals (e.g. using a brainwave response, which is more reliable and direct than a startle reflex) and applying this to humans.

DISCLOSURE

Technical Problem

This invention, having been devised in order to resolve the problems described above, has the objective of providing a tinnitus testing apparatus and tinnitus testing method using same, whereby, by using the examinee's brain wave response, which is a more reliable and direct response than the startle reflex, 1) it is possible to effectively measure tinnitus even in the elderly and infants, whose effective cooperation in testing cannot be obtained or who have an inadequate understanding of the test procedures; and 2) the objectivity and reliability of the test can be assured.

A further objective of this invention is to provide a method of tinnitus testing whereby an accurate test optimized for each individual can be conducted based on each patient's degree of hearing loss, tinnitus frequency and tinnitus amplitude.

This relates to a method wherein the information verified by the above-describe tinnitus testing apparatus and method is optimized for the patient, i.e. optimal stimulus conditions are identified for each individual patient's hearing and tinnitus levels so that more accurate testing is conducted under optimized conditions.

An additional objective of this invention is to provide a testing method that enables more accurate testing to be performed by secondarily re-verifying the tinnitus test result of the initial test.

This relates to the re-confirmation of the information yielded by the above-described tinnitus testing apparatus and method, i.e. the authentication of results by secondary reconfirmation that there was no error in the results, by double-checking the test results and minimizing the likelihood that they are due to error in testing.

Technical Solution

In order to solve said problem, the tinnitus testing apparatus of this invention comprises a control part that in turn comprises: an auditory stimulus generation part that can generate a stimulus; and an AEP acquisition and amplitude measurement part that can acquire auditory evoked potential (AEP) brain waves of a examinee due to said stimulus and measure the specific amplitude of said acquired brainwaves; wherein said auditory stimulus is one or more of: a 1st stimulus containing continuous noise and pulse noise; and a 2nd stimulus containing pulse noise and continuous noise with a silent gap.

It is preferable that the specific amplitude of said brainwave be N1-P2. It is also preferable that said 1st stimulus and said 2nd stimulus be presented in a random sequence.

Preferably, said tinnitus testing apparatus should further comprise an optimal stimulus selecting part whereby the frequency and amplitude of said continuous noise can be optimized based on the examinee.

Said optimal stimulus selecting part should preferably be configured to cause said stimulus generation part to transform the frequency of said continuous noise within an arbitrary range that includes the tinnitus frequency, based on the tinnitus frequency according to the examinee as confirmed via a tinnitogram frequency match, and the frequency of said continuous noise should be set by selecting a frequency having a maximum N1-P2 amplitude based on the N1-P2 amplitude measured by said AEP acquisition and amplitude measurement part, for each respective frequency.

Said optimal stimulus generation part should preferably be configured to cause said stimulus generation part to transform the loudness of said continuous noise within an arbitrary range that includes the loudness of the continuous noise, based on the tinnitus loudness of the examinee as confirmed via a tinnitogram loudness match, and the loudness of said continuous noise should preferably be set by initially selecting a loudness having a maximum N1-P2 amplitude based on the N1-P2 amplitude measured by said AEP acquisition and amplitude measurement part, for each respective loudness.

Said tinnitus testing apparatus should preferably also comprise a secondary tinnitus verification part, wherein said secondary tinnitus verification part is configured to enable said stimulus generation part to convert the gap between said silent gap and startle reflex within an arbitrary range based on a specific time, and wherein, based on the N1-P2 amplitude value measured for each respective interval by said AEP acquisition and amplitude measurement part: if there is a proportional change in N1-P2 amplitude, the patient is judged to have tinnitus; if there is a change in N1-P2 amplitude but no proportional trend is confirmed, the reliability of the test is judged to be poor; and if there is no change in N1-P2 amplitude, the patient is confirmed to be free of tinnitus.

Said tinnitus testing apparatus should preferably further comprise a G/N ratio calculation part that calculates the G/N ratio of the amplitude of N1-P2 response evoked by gap stimulus (G), due to said 2nd stimulus, to the amplitude of N1-P2 response evoked by no gap stimulus (N), due to said 1st stimulus.

Said tinnitus testing apparatus should preferably further comprise: a sound pressure level measuring device, one side whereof is connected to said stimulus generation part, for calibrating said stimulus generation part; an amplifier one side whereof is connected to said stimulus generation part and the other side whereof is connected to a headphone or earphone; and an output part and input part that are linked to said control part; wherein said output part can output said stimulus, the N1-P2 amplitude measured based on said stimulus, and said G/N ratio; and wherein said input part can select said stimulus.

In addition, to solve the above-described problem, this invention provides a tinnitus testing method comprising: (a) a step wherein one or more of a plurality of auditory stimuli are selected; (b) a step wherein the N1-P2 amplitude(s) of the examinee based on the selected stimuli are measured and averaged in real time; and (c) a step wherein based on the measured N1-P2 amplitude, the G/N ratio of the N1-P2 amplitude value for said 2nd stimulus to the N1-P2 amplitude value for said 1st stimulus is calculated.

It is preferable that said plurality of auditory stimuli be one or more from among: a 1st stimulus including a continuous noise and pulse noise; and a 2nd stimulus containing a pulse noise and continuous noise having a silent gap.

It is preferable that the testing method further comprise (d) a step wherein the presence or absence of tinnitus in the examinee is determined by comparing the calculated GIN ratio to a specified standard value.

It is preferable that said specified standard value be determined based on a clinically significant standard value of the G/N ratio, and that the examinee be judged to suffer from tinnitus if said ratio is greater than said standard value.

Advantageous Effects

Inasmuch as there are currently no apparatus or methods for objectively determining the presence or absence of tinnitus electrophysiologically, or specifically based on brain waves generated in response to an auditory stimulus, either in Korea or worldwide, this invention presents a very effective apparatus and method for the objective evaluation of tinnitus.

According to this invention, by using the examinee's brain wave response, which is a more objective reaction than the subjective tinnitograms that have previously been used to determine the presence or absence of tinnitus, 1) it is possible to effectively measure tinnitus even in the elderly and infants, whose effective cooperation in testing cannot be obtained or who have an inadequate understanding of the test procedures; and 2) for determining the presence or absence of tinnitus occurring after noise exposure or accident, the objectivity and reliability of the test can be assured. In short, this invention presents an apparatus and method that overcome the limits of the methods of the prior art that were based on behavioral response.

Furthermore, unlike the subjective tinnitus tests of the prior art, this invention enables tinnitus patients and tinnitus-free people to be distinguished by an objective test. As a result, it is expected that this invention will be a very useful test for clinical otolaryngological treatment. In particular, according to this invention, it can be used as a means for proving the presence or absence of tinnitus, so as to enable patients suffering from pain due to tinnitus after an industrial or traffic accident to obtain appropriate compensation and treatment; in addition, it enables the extent to which tinnitus has been alleviated after treatment to be objectively proven in patients who have undergone tinnitus treatment.

In addition, according to this invention, a testing method is provided whereby more accurate testing can be performed for each individual, matched to the patient's degree of hearing loss, tinnitus frequency and tinnitus loudness.

In addition, according to this invention, it is made possible to provide an apparatus and method whereby errors in test results can be minimized by conducting a second re-verification of initial results that indicate the presence or absence of tinnitus.

The effect of this invention, compared to the testing methods of the prior art (including the methods of the prior art for testing of both animals and humans), can be summarized as follows.

Compared to the method of the prior art for testing animals (i.e. the method published by Turner in 2006 using the startle reflex), this invention has the advantages, first, of enabling more direct measurement of the process of tinnitus perception, since in terms of the path of transmission along the auditory nerve, the reaction path is shorter than in the case of a startle reflex. Second, because brainwaves have greater reproducibility than a startle reflex and are affected by fewer variables, the test result is more accurate. Third, because the startle reflex in higher animals can easily become habitual, the longer the test goes on the greater is the likelihood that the reaction will be reduced; in contrast, habitualization does not occur with brain waves. Fourth, although it is quite difficult to quantitatively measure the startle reflex in humans, the amplitude and latency period of brain waves in humans can be measured quantitatively.

In addition, when compared to the human testing method of the prior art (i.e. the subjective tinnitogram test), the advantages of this invention are, first, that while the method of the prior art is a subjective test requiring the cooperation of the examinee, this invention is an objective test that is not affected by the patient's cooperation. Thus, it will play an important role when objective proof is needed or cooperation is difficult, such as in the cases of children, the elderly, or victims of industrial accidents. Second, while the results of the subjective test of the prior art can vary depending on the particulars of the patient's complaint, this invention has the advantage of being more accurate and reliable because it is objective.

DESCRIPTION OF DRAWINGS

FIG. 1(a) is a graph measuring the startle reflex in animals for auditory stimulus with no silent gap; FIG. 1(b) is a graph measuring the startle reflex in animals for auditory stimulus with a silent gap.

FIG. 2 is a graph showing in detail the N1 evoke d response and P2 evoked response measured by the tinnitus testing apparatus according to one embodiment of this invention.

FIG. 3(a) is a graph showing the N1-P2 reaction measured when applying a continuous noise and pulse noise to a tinnitus-free normal human in the absence of a silent gap; FIG. 3(b) is a graph showing the N1-P2 reaction measured when applying a continuous noise and pulse noise to a tinnitus-free normal human with a silent gap.

FIG. 4 is a schematic view of the tinnitus testing apparatus according to one embodiment of this invention.

FIG. 5 is a graph showing the average values of the N1-P2 amplitude with respect to the 1st stimulus and the N1-P2 amplitude with respect to the 2nd stimulus using the tinnitus analysis apparatus according to one embodiment of this invention on a group of tinnitus-free normal persons.

FIG. 6 is a graph showing the average values of the N1-P2 amplitude with respect to the 1st stimulus and the N1-P2 amplitude with respect to the 2nd stimulus using the tinnitus analysis apparatus according to one embodiment of this invention on a group of tinnitus patients.

FIG. 7 is a graph showing the respective average values upon calculating the GIN ratios for the normal group and the patient group.

FIG. 8 is a diagram of the method of setting the optimized frequency for the continuous noise for each patient by means of the optimal stimulus selecting part of the tinnitus testing apparatus according to one embodiment of this invention.

FIG. 9 is a diagram of the method of setting the optimized loudness of the continuous noise for each patient by means of the optimal stimulus selecting part of the tinnitus testing apparatus according to one embodiment of this invention.

FIG. 10 is a diagram of the method of performing secondary verification of the presence or absence of tinnitus by means of the secondary tinnitus verification part of the tinnitus testing apparatus according to one embodiment of this invention.

MODE FOR INVENTION

Hereinbelow, a preferred embodiment of the apparatus for testing tinnitus using brain waves, and of the method of tinnitus testing using same, will be described with reference to the attached drawings. In the process, the thickness of lines or size of components in the drawings may be exaggerated for clarity and convenience of explanation. In addition, the terms described below are defined with reference to the functionality of this invention; this may differ depending on the intentions or habits of the user or operator. Therefore, the definitions of these terms must be determined on the basis of the overall content of this specification.

In this specification, a method and apparatus are described for more objectively measuring the presence or absence of tinnitus by measuring the N1 and P2 reactions and the amplitude between N1-P2, but it is significant that, inasmuch as diverse types of brain waves not specifically mentioned in this specification, such as wave I, II, III, IV, V, P300, etc., exhibit similar appearances to the n1 and P2 reactions, a method and apparatus is feasible that uses this fact to more objectively measure the presence or absence of tinnitus.

EMBODIMENTS

FIG. 2 is a graph showing in detail the N1 evoke d response and P2 evoked response measured by the tinnitus testing apparatus according to one embodiment of this invention.

When an auditory stimulus such as sound is applied to the human body, brainwave reactions occur including the Auditory Brain-stem Response (ABR), Middle Latency Response (MLR) and Late Latency Response (LLP).

Here the Middle Latency Response denotes a reaction occurring between approximately 15 and 50 msec after an auditory stimulus, and Late Latency Response denotes a reaction occurring from approximately 75 to 200 msec, and more specifically from about 80 to 100 msec, after the auditory stimulus; these reactions occur in the central auditory pathway.

The N1 and P2 reactions correspond to the Late Latency Response; as described below in this specification, by measuring the N1 and P2 reactions and the N1-P2 amplitude, the presence or absence of tinnitus can be measured more objectively.

Reviewing in detail, in humans, measurement of the startle reflex as is done with the animal testing methods of the prior art is difficult and also inappropriate, since habitualization can easily occur. Accordingly, in the method and apparatus for tinnitus testing according to one embodiment of this invention, the auditory evoked response is used in place of the startle reflex as the primary outcome measure. The auditory evoked response is considered to originate in the central auditory pathway, which includes the primary auditory cortex. Thus, this has a similar character to the startle reflex measured in animals, since if a small auditory stimulus is applied, the N1-P2 reaction amplitude is reduced, and if a large auditory stimulus is applied, the N1-P2 reaction amplitude is increased. However, N1-P2 is more accurate and has greater reproducibility than the startle reflex, and also differs in that there is no reduction in reaction due to habitualization.

FIG. 3(a) is a graph showing the N1-P2 reaction measured when applying a continuous noise and pulse noise to a tinnitus-free normal human in the absence of a silent gap; FIG. 3(b) is a graph showing the N1-P2 reaction measured when applying a continuous noise and pulse noise to a tinnitus-free normal human with a silent gap.

Referring to FIG. 3, the N1 reaction can be measured about 100 msec after the auditory stimulus has occurred. In this case, for normal persons without tinnitus, if there is no silent gap, then just as in the case of the startle reflex, a high N1-P2 amplitude is measured; however, if there is a silent gap, a lower N1-P2 amplitude is measured. Because tinnitus-free patients can perceive the silent gap, the brain wave reaction to the pulse sound that occurs subsequently is reduced. In contrast, in the case of a patient with tinnitus, because the silent gap is filled by the tinnitus, the patient does not perceive there to be a silent gap, and therefore the brain wave reaction to the pulse sound that occurs subsequently is identical.

Therefore, the tinnitus testing apparatus and method according to one embodiment of this invention can objectively distinguish between patients with and without tinnitus by using the above-described principles.

The tinnitus testing apparatus according to one embodiment of this invention will now be described with reference to FIG. 4.

The control part (100) comprises an auditory stimulus generation part (110), AEP acquisition and amplitude measurement part (120), and GIN ratio calculation part (130).

The control part (100) processes data and any storage-capable medium is sufficient; the stimulus generation part (110), AEP acquisition and amplitude measurement part (120) and G/N ratio calculation part (130) are simply functional divisions for the purpose of explaining this invention, and it should be borne in mind that there is no requirement to divide these functions or divide the information processing apparatus. In addition, with regard to the "generation" of the auditory stimulus, it must be understood that the stimulus need not solely be produced by the control part (100) but that the concept of importing the auditory stimulus via an external memory medium is also included.

The stimulus generation part (110) generates the auditory stimulus, and this stimulus may comprise a 1st stimulus that includes a continuous noise and pulse noise, and a 2nd stimulus that includes a pulse noise and continuous noise with a silent gap.

The 1st stimulus and/or 2nd stimulus generated by the stimulus generation part (110) may be played to the examinee (1) via an amplifier (300) and headphone (or earphone), etc. Calibration can then be performed by connecting the stimulus generation part with a sound level meter (200) such as a probe microphone that measures the sound pressure next to the ear drum within the outer ear, so as to transmit a stimulus of an intensity appropriate to the examinee.

The stimulus for generating the N1 and P2 reactions in humans can be described in greater detail as follows. As described hereinabove, the 1st stimulus comprises a continuous noise and pulse noise; the 2nd stimulus comprises a continuous noise with silent gap and a pulse noise.

The N1 and P2 reactions of the examinee (1) to the auditory stimulus are measured by the AEP acquisition and amplitude measurement part (120). Therefore, unlike the methods and apparatus of the prior art, an objective response can be measured even if the examinee (1) exhibits no particular physical reaction. The AEP acquisition and amplitude measurement part (120) can measure the N1-P2 amplitude as well as the N1 and P2 reactions.

The G/N ratio calculation part (130) acts to calculate the G/N ratio of the N1-P2 amplitude for said 2nd stimulus to the N1-P2 amplitude for said 1st stimulus.

In other words, the G/N ratio represents either the quotient of the N1-P2 amplitude for the 2nd stimulus, which includes a silent gap, divided by the N1-P2 amplitude for the 1st stimulus, which does not include a silent gap, or 100 times this value.

Significantly, in the ideal case, the G/N ratio for normal persons without tinnitus will be lower than the standard value, and the G/N ratio for patients with tinnitus will be higher than the standard value (approaching 1 or 100%).

The control part (100) links the output part (130) and input part (140). The output part (130) can depict the stimulus used in the experiment, the N1-P2 amplitudes measured for said stimuli, and said G/N ratio, as a graph or as certain numeric data. A command can be selected via the input part (140) whereby the stimulus is selected or the stimulus is played to the examinee (1), or the experimental results are analyzed. In addition, the results of a subjective tinnitus determination method of the prior art can be entered via the input part (140) and output together with the results according to the apparatus according to one embodiment of this invention and compared.

In order to measure the presence or absence of tinnitus in a examinee using the tinnitus testing apparatus according to one embodiment of this invention, the type of auditory stimulus, such as 1st stimulus or 2nd stimulus, is first selected by means of the input part (140). Here it is significant that with regard to the stimulus, the loudness and frequency of the continuous noise, the intervals between pulse noise and silent gap, and the loudness and duration of the pulse noise, can also be adjusted.

Next, if the stimulus selected by manipulation of the control part (100) is played to the examinee (1), the consequent N1-P2 reaction and amplitude, etc., of the examinee (1) are measured by means of the AEP acquisition and amplitude measurement part (120). Here it is significant that the N1-P2 amplitude for the 1st stimulus and the N1-P2 amplitude for the 2nd stimulus can be stored either temporarily or permanently in the control part (100).

Next, based on the measured N1-P2 amplitudes, the GIN ratio calculation part (130) calculates the GIN ratio of the N1-P2 amplitude for said 2nd stimulus to the N1-P2 amplitude for said 1st stimulus.

Next, the control part (100) determines whether the examinee suffers from tinnitus by comparing the calculated GIN ratio to the standard value. Here, it is preferable that said standard value be a clinically significant standard value set based on experiments and statistics, and may e.g. be between 0.7 and 0.9. If said calculated ratio is greater than said standard value, the examinee is judged to have tinnitus.

The results measured by this method can be reviewed as follows.

FIG. 5 is a graph showing the average values of the N1-P2 amplitude with respect to the 1st stimulus and the N1-P2 amplitude with respect to the 2nd stimulus using the tinnitus analysis apparatus according to one embodiment of this invention on a group of tinnitus-free normal persons (7 male, 1 female, average age: 29.4±3.0).

FIG. 6 is a graph showing the average values of the N1-P2 amplitude with respect to the 1st stimulus and the N1-P2 amplitude with respect to the 2nd stimulus using the tinnitus analysis apparatus according to one embodiment of this invention on a group of patients with tinnitus (3 male, 1 female, average age: 38.0±23.1).

FIG. 7 is a graph showing the respective average values upon calculating the GIN ratios for the normal group and the patient group.

Referring to FIGS. 5 through 7, it is evident that the GIN ratio in the normal group was measured as comparatively low, at 79.2±14.7 (average approximately 78%), and the G/N ratio in the patient group was measured as comparatively high, at 5.6±19.9 (average approximately 97%). Specifically, it is preferable that the standard value for determining the presence or absence of tinnitus be a clinically significant value (e.g. 70% to 90%); if the G/N ratio of examinees whose tinnitus status is unknown is greater than said standard value, the examinee is judged to have tinnitus, thereby enabling the presence or absence of tinnitus to be determined more objectively.

Using the above-described apparatus and testing method, the presence or absence of tinnitus can be verified objectively. However, in order to increase the reliability of the test results and minimize the likelihood of error, a process of optimization is undertaken for each individual. Because the loudness and frequency of the tinnitus as subjectively felt by the patient can differ from what is actually perceived in the patient's brain, a process of optimizing the test for the conditions perceived in the brain is needed in order to further maximize the difference in results between normal examinees and tinnitus patients. This is because, in the absence of optimization, even if tinnitus is actually perceived in the brain, there is a possibility that the tinnitus will not be confirmed by the brainwave result.

To this end, the tinnitus testing apparatus according to one embodiment of this invention can additionally be furnished with an optimal stimulus selecting part (160).

The optimal stimulus selecting part (160) is intended for optimization of the stimulus, and specifically the frequency and loudness of the continuous stimulus, and thus is an element that can optimize the tinnitus frequency and tinnitus loudness, which differ for each patient.

Reviewing the functionality of the optimal stimulus selecting part (160), the optimal stimulus selecting part (160) enables the stimulus generation part (110) to transform the frequency of the generated continuous noise to the tinnitus frequency, ±1 KHz, or ±2 KHz, based on the tinnitus frequency for each patient as confirmed via tinnitogram frequency match. The pulse noise is kept at a frequency of about 1 KHz. Then for each case, the frequency of the continuous noise is selected as the frequency with the greatest amplitude when compared to the N1-P2 amplitude measured via the AEP acquisition and amplitude measurement part (120) (the frequency with the greatest amplitude being the one closest to the tinnitus frequency of the tinnitus patient).

For example, referring to FIG. 8, when a stimulus has been applied having a continuous noise of 8 kHz, 9 kHz, or 10 kHz with a silent gap and a pulse noise (approx. 1 kHz tone), the N1-P2 amplitude is judged to be greatest when the frequency of the continuous noise is 8 kHz, and therefore in this case it is evident that 8 kHz is most appropriate as the frequency of the continuous noise.

Thereafter, the optimal stimulus selection part (160) enables the stimulus generation part (110) to transform the generated loudness of the continuous noise to ±1 dB SL, ±2 dB SL, in 1 dB SL units, based on the selected frequency of the continuous noise and the loudness confirmed by means of a tinnitogram loudness match. The pulse noise is kept at a frequency of about 1 KHz. Then for each case, the loudness of the continuous noise is selected as the loudness with the greatest amplitude when compared to the N1-P2 amplitude measured via the AEP acquisition and amplitude measurement part (120) (the loudness with the greatest amplitude being the one closest to the tinnitus loudness of the tinnitus patient).

For example, referring to FIG. 9, when a stimulus has been applied having a continuous noise of 8 kHz with a silent gap and a pulse noise (approx. 1 kHz tone), the N1-P2 amplitude is judged to be greatest when the loudness of the continuous noise has reached an appropriate level, and therefore in this case it is evident that said appropriate level is most appropriate as the loudness of the continuous noise.

By means of this process, the continuous noise frequency and loudness optimized by the optimal stimulus selecting part (160) are applied to the 1st stimulus and 2nd stimulus, and as described hereinabove, by measuring the N1-P2 amplitude, it is made possible to more precisely measure the presence or absence of patients with the tinnitus testing apparatus according to one embodiment of this invention. The process up to this point is defined as the 1st tinnitus verification process.

In the use of the tinnitus testing apparatus as described, even if the tinnitus detection result is incorrect due to an accidental brain wave abnormality, there is no method for verifying whether there has been an error in the measurement process. However, this problem can be addressed by going through a secondary verification process added to the primary verification.

To this end, the tinnitus testing apparatus according to one embodiment of this invention can additionally be furnished with a secondary tinnitus verification part (not shown).

The secondary tinnitus verification part is intended for the more accurate verification of the presence or absence of tinnitus, and is an element that can further improve the reliability of the test results.

Reviewing the functionality of this secondary tinnitus verification part, the secondary tinnitus verification part enables the stimulus generation part (110) to transform the generated silent gap and pulse noise interval by ±20 msec, ±40 msec, based on a specific time (e.g. 50 msec). Then for each case, the N1-P2 amplitude measured by means of the AEP acquisition and amplitude measurement part (120) is compared.

By means of this result, if the N1-P2 amplitude value is changed, the patient is determined to be normal, and if the measured N1-P2 amplitude value is constant, a final determination is made that the patient has tinnitus.

For example, referring to FIG. 10, if the silent gap and inter-pulse intervals are 50 msec, 30 msec, 10 msec, then in the case of a patient with tinnitus, a constant N1-P2 value will be measured, while in the case of a normal tinnitus-free patient, the N1-P2 amplitudes will gradually undergo a proportionate decrease.

In normal persons, the difference in brain waves trends gradually and proportionally upward as the interval position is optimized, based on the dose response relationship; therefore, by this principle, even if there have been some accidental abnormal brain waves once or twice in the testing, the likelihood that the overall proportional trend itself will break down is reduced. In addition, because a case which the overall proportional trend does break down would indicate low reliability of the test, it could be readily recognized as an error in the measurement process. Thus, by means of this process, the errors in testing can be positively reduced and the reliability of the test can be enhanced.

Hereinabove, this invention has been depicted and described in relation to a specific embodiment; however, this invention is not limited thereto, and it will be readily evident to a person of ordinary skill in the art that this invention can be altered and converted in various ways without departing from the scope of this invention as laid out in the claims below.

INDUSTRIAL APPLICABILITY

The apparatus of this invention for testing tinnitus using brainwaves, and the tinnitus testing method using same, can be applied and used effectively in all fields of industry related to medical devices, due to the advantage it affords of being able to more objectively evaluate the presence or absence of tinnitus.

The invention claimed is:

1. A tinnitus testing apparatus that tests for tinnitus in a patient, the tinnitus testing apparatus comprising:
a control system comprising at least one processor, the at least one processor which executes one or more processor-executable instructions that cause the at least one processor to:
generate an auditory stimulus having an adjustable frequency, said auditory stimulus including a 1st auditory stimulus containing continuous noise and pulse noise and a 2nd auditory stimulus containing pulse noise and continuous noise with a silent gap;
receive signals that represent auditory evoked potential (AEP) brainwaves of the patient due to said auditory stimuli;
measure an N1-P2 amplitude of said received signals representative of the AEP brainwaves;
selectively vary the adjustable frequency of said continuous noise in the 1st auditory stimulus and of said continuous noise in the 2nd auditory stimulus output during a first time period;
determine a frequency for said continuous noise in the 1st auditory stimulus and of said continuous noise in the 2nd auditory stimulus based at least in part upon a maximum N1-P2 amplitude from the signals representative of the AEP brainwaves during the first time period;
during a second time period adjust the adjustable frequency of said continuous noise in the 1st auditory stimulus and of said continuous noise in the 2nd auditory stimulus that is output by the tinnitus testing apparatus based at least in part upon the determined frequency;
determine a G/N ratio of the N1-P2 amplitude of an N1-P2 response evoked by said 2nd stimulus to the N1-P2 amplitude of an N1-P2 response evoked by said 1st stimulus; and
at least one earphone, the at least one earphone which is communicatively coupled to the control system, the at least one earphone which generates audible sound based upon at least one of the 1st auditory stimulus and the 2nd auditory stimulus during the first time period and which generates audible sound based upon at least one of the 1st auditory stimulus and the 2nd auditory stimulus during the second time period.

2. The tinnitus testing apparatus of claim 1, wherein the at least one processor executes one or more processor-executable instructions that cause the at least one processor to change the adjustable frequency of said continuous noise in the 1st auditory stimulus and of said continuous noise in the 2nd auditory stimulus within an arbitrary range during the first time period in which the arbitrary range includes a tinnitus frequency as confirmed via a tinnitogram frequency match.

3. The tinnitus testing apparatus of claim 2, wherein the at least one processor executes one or more processor-executable instructions that cause the at least one processor to:
modify an adjustable loudness of said continuous noise in the 1st auditory stimulus and of said continuous noise in the 2nd auditory stimulus within an arbitrary range during the first time period in which the arbitrary range includes a tinnitus loudness as confirmed via a tinnitogram loudness match,
determine a loudness of said continuous noise in the 1st auditory stimulus and of said continuous noise in the 2nd auditory stimulus based at least in part upon the maximum N1-P2 amplitude measured during the first time period, and
during the second time period, set the adjustable loudness of said continuous noise in the 1st auditory stimulus and of said continuous noise in the 2nd auditory stimulus based at least in part upon the determined loudness.

4. A tinnitus testing apparatus that tests for tinnitus in a patient, the tinnitus testing apparatus comprising:
a control system comprising at least one processor, the at least one processor which executes one or more processor-executable instructions that cause the at least one processor to:
for each of a plurality of intervals,
generate an auditory stimulus having an adjustable frequency, said auditory stimulus including a 1st auditory stimulus containing continuous noise and pulse noise and a 2nd auditory stimulus containing pulse noise and continuous noise with a silent gap;

receive signals that represent auditory evoked potential (AEP) brainwaves of the patient due to said auditory stimuli;

measure an N1-P2 amplitude of said received signals representative of the AEP brainwaves;

selectively vary the adjustable frequency of said continuous noise in the 1st auditory stimulus and of said continuous noise in the 2nd auditory stimulus output during a first time period;

determine a frequency for said continuous noise in the 1st auditory stimulus and of said continuous noise in the 2nd auditory stimulus based at least in part upon a maximum N1-P2 amplitude from the signals representative of the AEP brainwaves during the first time period; and during a second time period adjust the adjustable frequency of said continuous noise in the 1st auditory stimulus and of said continuous noise in the 2nd auditory stimulus that is output by the tinnitus testing apparatus based at least in part upon the determined frequency; and at least one earphone, the at least one earphone which is communicatively coupled to the control system, the at least one earphone which generates audible sound based upon at least one of the 1st auditory stimulus and the 2nd auditory stimulus during the first time period and which generates audible sound based upon at least one of the 1st auditory stimulus and the 2nd auditory stimulus during the second time period, wherein the at least one processor executes one or more processor-executable instructions that cause the at least one processor to, for each 2nd auditory stimulus in each of the plurality of intervals, alter the duration of the continuous noise between said silent gap and pulse noise within an arbitrary range based on a specific time, and wherein, based on the measured N1-P2 amplitude value measured for each respective interval of the plurality of intervals:

if there is a proportional change in N1-P2 amplitude with respect to the duration of the continuous noise, the patient is judged to have tinnitus; if there is a change in N1-P2 amplitude but no proportional trend is confirmed, the a reliability of the test is judged to be poor; and if there is no change in N1-P2 amplitude, the patient is confirmed to be free of tinnitus.

5. The tinnitus testing apparatus of claim 4, wherein the at least one processor executes one or more processor-executable instructions that cause the at least one processor to determine a G/N ratio of the amplitude of N1-P2 response evoked by said 2nd stimulus to the amplitude of N1-P2 response evoked by said 1st stimulus.

6. The tinnitus testing apparatus of claim 5, wherein said tinnitus testing apparatus further comprises:

a sound pressure level measuring device, one side whereof is communicatively coupled to the control system, the sound pressure level measuring device which calibrates said generation of the auditory stimulus; and an amplifier that is communicatively coupled to said control system and to the at least one earphone.

7. The tinnitus testing apparatus of claim 1, wherein said tinnitus testing apparatus further comprises:

a sound pressure level measuring device, one side whereof is communicatively coupled to the control system, the sound pressure level measuring device which calibrates said generation of the auditory stimulus; and an amplifier that is communicatively coupled to said control system and to the at least one earphone.

* * * * *